United States Patent
Sudarsky et al.

(10) Patent No.: US 12,295,776 B2
(45) Date of Patent: May 13, 2025

(54) SYSTEM AND METHOD FOR AUTOMATIC LIGHT ARRANGEMENT FOR MEDICAL VISUALIZATION

(71) Applicant: SIEMENS HEALTHINEERS AG, Forchheim (DE)

(72) Inventors: Sandra Sudarsky, Bedminster, NJ (US); Kaloian Petkov, Lawrenceville, NJ (US)

(73) Assignee: Siemens Healthineers AG, Forchheim (DE)

( * ) Notice: Subject to any disclaimer, the term of this patent is extended or adjusted under 35 U.S.C. 154(b) by 470 days.

(21) Appl. No.: 17/648,698

(22) Filed: Jan. 24, 2022

(65) Prior Publication Data

US 2022/0287669 A1   Sep. 15, 2022

(51) Int. Cl.
*A61B 6/00* (2024.01)
*A61B 6/03* (2006.01)
(Continued)

(52) U.S. Cl.
CPC ............ *A61B 6/5223* (2013.01); *A61B 6/032* (2013.01); *A61B 6/469* (2013.01); *A61B 6/5205* (2013.01); *G06T 15/506* (2013.01)

(58) Field of Classification Search
CPC .......... A61B 6/03; A61B 6/032; A61B 6/466; A61B 6/469; A61B 6/5205; A61B 6/5223;
(Continued)

(56) References Cited

U.S. PATENT DOCUMENTS 5,870,097 A    2/1999  Snyder et al.
6,847,361 B1 *  1/2005  Kitsutaka ................ G06T 15/60
                                                   463/31
(Continued)

FOREIGN PATENT DOCUMENTS

CN        101014983 A    8/2007
CN        110132166 A    8/2019
(Continued)

OTHER PUBLICATIONS

Marschner, S. R., & Greenberg, D. P. (Jan. 1997). Inverse lighting for photography. In Color and Imaging Conference (vol. 5, pp. 262-265). Society of Imaging Science and Technology. (Year: 1997).*

(Continued)

*Primary Examiner* — Andrae S Allison
*Assistant Examiner* — Emmanuel Silva-Avina

(57) ABSTRACT

An automatic light arrangement for medical visualization includes: providing a medical 3D image (D), providing spatial information about a region of interest (R) in this 3D-image (D) and spatial information about a virtual camera (C), determining a plurality of possible arrangements for light sources (L) by using depth information based on the 3D image (DI) together with the spatial information about the region of interest (R) in this image and the spatial information about the virtual camera (C), wherein valid arrangements are those where shadows (S) on the region of interest (R) are below a predefined threshold, and/or wherein the determination or arrangements is based on a number of predefined perceptual metrics applied specifically to the regions of interest, prioritizing the determined arrangements, and choosing the arrangement with the best prioritization.

18 Claims, 7 Drawing Sheets

(51) Int. Cl.
*A61B 6/46* (2024.01)
*G06T 15/50* (2011.01)

(58) Field of Classification Search
CPC ....... G06T 15/506; G06T 15/08; G06T 15/60;
G06T 19/00; G06T 2210/41; G06T 2210/12
USPC .......................................................... 382/131
See application file for complete search history.

(56) References Cited

U.S. PATENT DOCUMENTS

| | | | |
|---|---|---|---|
| 7,839,402 | B2 | 11/2010 | Dekel et al. |
| 9,330,485 | B2* | 5/2016 | Wahrenberg ............ G06T 15/08 |
| 2011/0069068 | A1* | 3/2011 | Ha .......................... G06T 15/60 |
| | | | 345/426 |
| 2016/0063758 | A1* | 3/2016 | Schroecker ............. G06F 16/51 |
| | | | 345/426 |
| 2016/0381256 | A1* | 12/2016 | Aguirre-Valencia ....................... |
| | | | H04N 13/30 |
| | | | 348/46 |
| 2017/0367785 | A1 | 12/2017 | Munari |
| 2018/0260997 | A1 | 9/2018 | Petkov et al. |
| 2018/0317864 | A1 | 11/2018 | Sra et al. |
| 2018/0360425 | A1* | 12/2018 | Wahrenberg .......... G06T 7/0012 |
| 2019/0147645 | A1 | 5/2019 | Mory et al. |
| 2019/0254143 | A1 | 8/2019 | Hallack et al. |
| 2023/0070102 | A1* | 3/2023 | Mory .................... G06T 15/503 |

FOREIGN PATENT DOCUMENTS

| | | |
|---|---|---|
| EP | 3373245 A2 | 9/2018 |
| EP | 3557182 A1 | 10/2019 |
| WO | 2007048197 A1 | 5/2007 |

OTHER PUBLICATIONS

Halle, Michael, and Jeanette Meng. "Lightkit: A lighting system for effective visualization." IEEE Visualization, 2003. VIS 2003 . . . IEEE, 2003. (Year: 2003).*
Tao, Yubo, et al. "Structure-aware lighting design for volume visualization." IEEE Transactions on Visualization and Computer Graphics 18.12 (2012): 2372-2381. (Year: 2012).*
Comaniciu D, Engel K, Georgescu B, Mansi T. Shaping the future through innovations: From medical imaging to precision medicine. Med Image Anal. 2016;33:19-26.
European Search Report for European Application No. 21161885.5 mailed Sep. 14, 2021.
Louis Bavoil, Miguel Sainz, Rouslan Dimitrov,"Image-space horizon-based ambient occlusion", Computer Science, SIGGRAPH '08, 2008 (Slides and abstract).
P. Poulin, K. Ratib and M. Jacques, "Sketching shadows and highlights to position lights," Proceedings Computer Graphics International, Hasselt and Diepenbeek, Belgium, 1997, pp. 56-63.
Vazquez, "Automatic Light Source Placement for Maximum Visual Information Recovery," Computer Graphics Forum 26(2):143-156, Jun. 2007.
Y. Zhang and K. Ma, "Lighting Design for Globally Illuminated Volume Rendering," in IEEE Transactions on Visualization and Computer Graphics, vol. 19, No. 12, pp. 2946-2955, Dec. 2013.
Zhou, J., Wang, X., Cui, H. et al. Topology-aware illumination design for volume rendering. BMC Bioinformatics 17, 309 (2016).
Qin An et al: "Fast volume Rendering of Region of Interest in Medical Images Based on Illumination Sphere Index", Jan. 15, 2010 (includes English abstract).

* cited by examiner

SYSTEM AND METHOD FOR AUTOMATIC LIGHT ARRANGEMENT FOR MEDICAL VISUALIZATION

RELATED APPLICATION

This application claims the benefit of 21161885.5, filed Mar. 10, 2021, which is hereby incorporated by reference in its entirety

FIELD

The embodiments pertain to a system and a method for automatic light arrangement for medical images, especially automatic light placement for medical visualization based on regions of interest.

BACKGROUND

Light design is an important area of research that focuses on the importance of complex light setups in visualization. Proper illumination is indispensable in medical visualization where accurate rendering of the patient's anatomy is paramount. However, finding an optimal set up is not trivial. Despite important advances in the area of light design, finding the best parameters to illuminate a scene remains a manual and time-consuming task.

Cinematic Rendering ("CR") is a 3D visualization technology that can produce photorealistic images from traditional Computer Tomography (CT) or Magnetic Resonance (MR) volumes (see e.g., Comaniciu D, et al. "Shaping the future through innovations: From medical imaging to precision medicine", Med Image Anal. 2016; 33:19-26). CR uses a global lighting model based on Monte Carlo path tracing to create realistic shading effects enhancing depth and shape perception of a volume dataset.

Typically, CR methods use high-dynamic range (HDR) light-maps to illuminate the scene in a natural way. These maps can be combined with synthetic lights to highlight special structures or illuminate internal organs. The orientation of these light-maps as well as the placement of the synthetic lights can provide valuable perceptual information about the depth, shape, and surface characteristics of the data.

The conventional approach to lighting design for volume rendering is based on setting the lighting parameters manually and modify them until the desired image is generated. As this process is time consuming and often requires some technical and aesthetic knowledge of lighting, several methods have been proposed to facilitate this task.

Poulin et al. ("Sketching shadows and highlights to position lights", Proceedings Computer Graphics International, Hasselt and Diepenbeek, Belgium, 1997, pp. 56-63) let the user specify shadows and highlights as desired properties on the final image. An inverse shading method is then used to determine the light sources positions to satisfy these constraints.

Zhou, J. et al. ("Topology-aware illumination design for volume rendering". BMC Bioinformatics 17, 309; 2016) discloses an illumination design for volume rendering—based on data topology. The objective of this approach is not to determine the optimal light position and direction but rather adjust lighting coefficients based on topological attributes, topological distance and topological saliency of the data.

Zhang and Ma ("Lighting Design for Globally Illuminated Volume Rendering", in IEEE Transactions on Visualization and Computer Graphics, vol. 19, no. 12, pp. 2946-2955, December 2013) apply a three-point lighting setup commonly used in photography to volume rendering. A key-light is setup based on analysis of the statistical distribution of surface normal of the entire volume dataset. A fill-light is used to illuminate the shadow areas in order to make the details in the shadow areas visible while a backlight is used to improve depth perception. This approach generates well-balanced images but does not take into account which areas are in shadow and which ones are in light. This can lead to images with strong shadows hiding important details of the data.

SUMMARY AND DESCRIPTION

It is the object to improve the known systems, devices and methods to facilitate an automatic light arrangement for medical visualization, especially in controlling a medical imaging system to set the optimum light arrangement.

This object is achieved by a method, a system, a control device, and a medical imaging system according to the claims.

A method according to one embodiment for light arrangement for medical visualization, especially for controlling a medical imaging system to set the optimum light arrangement, includes the following acts:

providing a medical 3D image, that could e.g., be a full 3D-image with voxels or also a sequence of 2D slice images describing a 3D volume, wherein this 3D image is a volumetric image including depth information or the possibility to compute depth information with a given camera view, providing spatial information about a region of interest in this image and a virtual camera (e.g., defined manually or detected automatically), optionally: providing information about a number of predefined artificial light sources (i.e., information what type(s) of light sources and especially how many light sources of this/these type(s) should be used), determining a plurality of possible arrangements for the light sources by using depth information based on the 3D image together with the spatial information about the region of interest in this image and the spatial information about the virtual camera (or a virtual observer), wherein valid arrangements are those where shadows on the region of interest are below a predefined threshold, prioritizing the determined arrangements, especially by using guidelines form photography, choosing the arrangement with the best prioritization.

These acts could be followed by the act:

rendering an image with shadows using the chosen arrangement of the light sources. However, once the light arrangements are set, the lighting calculation can be computed via well-known equations.

First of all, the 3D image-data (a 3D volume), the region of interest, the position of the virtual camera, and the type of the light sources have to be defined or at least be known for further determinations. This can be achieved automatically (e.g., by using preferences) or by manual selection by a user. Typically, these acts are state of the art, since choosing an image and an ROI and (manually) selecting and arranging light sources is common practice in the art. However, embodiments add the special features described in the following. Concerning the 3D-image, it is preferably defined as a sequence of 2D image slices from a medical scan which are often referred as a 3D volume. Alternatively, the 3D image can be constructed from mathematical/functional descriptions, it can be the result of computational simulations (e.g., molecular dynamics).

Regarding the provision of information of artificial light sources, positions of these light sources are not necessary information (because the arrangement is calculated in the course of the method). Preferred information is about the type of light sources forming the lighting arrangement. This act could be a simple predefinition that an individual type of light source (e.g., a key-light with a predefined intensity) should be used. The act could also be the provision of a light map with defined properties read from a memory device. However, this act could also include a user input about light sources to be used (e.g., a key-light and a fill-light). An information could also be hardwired to the method, e.g., "if there is no user input and no memory device available, use a key-light for the following acts". It should be noted that the number and type of light sources could be enhanced later, e.g., if additional light sources are added.

The virtual camera implies the knowledge of the camera angle, position, and orientation relative to the 3D volume and the ROI data.

A "region of interest" (ROI) is also no physical object, but a sample of data (a 3D region) within the dataset (volume) of the 3D image and especially not the whole 3D image. It can be defined by its position and voxel information at this position. Especially, the ROI could be taken as a polygonal selection inside the 3D image. For example, it could define the borders of an object (e.g., organ) under consideration. In the technical field of medicine, an ROI is a particular region (of image-data) that has been identified to provide important medical information. The concept of ROIs is commonly used in the literature of image processing and radiology. The ROIs could represent suspected tumors, aneurysms, etc.

In contrast to techniques that generate images having well balanced highlights, midtone, and shadow areas, what could lead to the drawback that these images could be well balanced while overshadowing important structures, the present embodiment has the advantage that it uses said ROIs and not just the whole image to compute the lighting.

The term "providing" here means that certain information is available for the method. It is not crucial how the data is provided. Thus "providing", especially means "reading an input", "reading a predefined parameter", "calculating" or "measuring".

The spatial information about the regions of interest are information about the position, orientation, and especially also the shape of the region of interest within the 3D image.

The spatial information about the virtual camera are information about the position and the viewing direction of the virtual camera (the viewing direction should point to the region of interest). Regarding calculations, it is preferred to consider only ROIs within the viewing frustum of the camera when computing the lighting. In this case, other ROIs could exist, but they are ignored until the camera is rotated to include them in the view.

Each of the spatial information could be provided as an input or a predefined parameter.

Spatial information about ROIs are preferably identified based on user selection, automatic detection, automatic segmentation, data analysis, user gaze tracking or 3D tracking of surgical instruments. For instance, spatial information could be defined as an area of high curvature. Areas of high curvature are usually structures that carry important information compared to homogeneous regions (or regions with low curvature) so they could be used are ROIs.

The term "light sources" includes any synthetic lighting that can be applied for artificial lighting of a reconstructed medical image. Such light source is preferably a key-light or a light-map (also known as "environment-map"), but also could especially be a spotlight or a fill-light. The light sources could include one single light source, only, or two or more light sources (e.g., "three-point lighting"), especially a key-light or a light-map combined with at least one spotlight and/or fill-light. A key-light is preferably modelled as a directional light that is infinitely away from the scene. It is especially defined as a direction vector, not having an exact position and tends to illuminate the entire scene from an infinitely distant place. The intensity of a preferred key-light is set to be 1 (unit respective to other lights). A light-map can be used instead of a key-light or together with a key-light. Preferably, a light-map is oriented such that the highest intensity (usually the sky) shines in the direction that would also be the direction of a key-light.

Especially, one or more light sources are selected from the group including key-lights, light-maps, fill-lights (to lighten up shadows), back-lights, and spot-lights. It should be noted that since the method refers to reconstruction of medical images, the light sources are not real light sources, but synthetic light sources commonly used for 3D rendering. Such light sources themselves are well known in the art.

For applying the method according to one embodiment, a number of light sources must be "provided", i.e., it must be clear what types of light sources are initially used and how many of a type. This could be achieved by a preference made by a predefinition or a user-input. However, light sources may also be provided by choosing or calculating them automatically. For example, it can be predefined that always a key-light with given characteristics (direction and shape of the light cone, intensity) is used. When the method detects that there is a shadow that is darker than a predefined threshold and cannot be softened by amending the position of the key-light, a fill-light or a spotlight could be added automatically.

The term "arrangement" (or "placement") means that the orientation and/or the position of a number of light sources is determined. This means that the position of a light source in the environment of the region of interest is provided (may also include an infinite distance) and the orientation of the light source in this environment, i.e., the vector of the main direction(s) of the beam(s), at least in the case of a non-omnidirectional light source.

For example, a light-map (a pre-rendered texture that stores information simulating a lighting environment) may be positioned in that the orientation of the lightmap is modified such that the alignment of the brightest region of the lightmap corresponds to the direction of the computed light. The arrangement is then the definition of the orientation of the light-map around the volume, i.e., the orientation of the light rays.

Regarding a key-light, a directional light or a headlight could be assumed. A directional light is also assumed to be infinitely far away, again only the orientation of the parallel light rays needs to be computed. For headlights, the position is important as light intensity becomes inversely proportional to the square of the distance.

Regarding a spotlight, it simulates light radiating from a single infinitely small point in space with specific orientation. It is especially chosen to illuminate a specific ROI when there is no configuration for which all ROIs could be illuminated by a key-light. The spotlight is then preferably placed near the given ROI and aimed in its direction.

Regarding a homogeneous, omni-directional light source, there is no need to define an orientation, since the light is emitted in all directions. However, the position has to be defined.

Concerning fill-lights (and spotlights), it is preferred that in the course of determining a plurality of possible arrangements, different intensities, and/or illumination angles are regarded, e.g., in nested loops, for different orientations different intensities and/or illumination angles are tested.

Fill-lights are usually used to light some portions of the scene that otherwise would remain dark. These lights are preferably modelled as spotlights having a position and direction and a certain opening angle so that only objects that are within a certain radius are lit. For these lights, the intensity is inversely proportional to the square of the distance to the object being illuminated while increasing the surface area covered (inverse square law). Knowing the size of the area that needs to be illuminated (in an ROI) and the distance to the fill-light, the proper intensity can be computed. If the fill-light (as a spotlight) is, e.g., placed at a distance d from the ROI, it will illuminate a surface area A of size $4\pi d^2$ with intensity $I_0/A$, where $I_0$ is the initial intensity of the fill-light and it is set of a value $I_0<1$ (relative to the intensity of the key-light).

Regarding the important act of determining the plurality of possible arrangements for the light sources, there are determined two or more possible arrangements. The arrangements should be different. It is preferred to use an inverse illumination technique for determination, well known in the art.

For the determination, the depth information based on the 3D image (provided in the 3D image or calculated) and spatial information about the region of interest in this image (clarifying the position of the ROI in the 3D image) is used for the determination of the position, orientation, and shape of the region of interest and of surrounding structures for the shadows. The spatial information about the virtual camera is used to determine how the region of interest is seen by the virtual camera and, e.g., also which shadows are relevant for the virtual camera, since shadows that are hidden by structures in the front cannot be seen by the virtual camera and are, therefore, of minor relevance.

The quality of the visual information of the image around each ROI can be determined based on some perceptual metric applied specifically to these areas, including how dark these areas are compared to the rest of the image. Some of these metrics can include the average luminance around the ROI. Other metrics described in more detail in "Automatic Lighting Design Using a Perceptual Quality Metric" by Shacked et al.

The "quality" of shadows in ROIs can be quantified by the radiance or brightness and/or the area that is shadowed and/or whether special points of the ROI are covered with shadows or not. To determine valid arrangements, the quantified "quality" of the shadows in the ROI(s) can be compared with a predefined threshold (could be a constant value or a map of values, each for a different position in the ROI). In the case, this threshold is undershot, e.g., the shadows are lighter or smaller than the threshold defined and not covering certain points in the ROI, the arrangement is a valid arrangement. Also, the "quality" of the shadows in the ROI(s) can be compared to the radiance other areas of the image, the darkest/brightest/median values of the image Preferably, there are certain boundary conditions for possible positions of the light source, and not the whole space around the region of interest is used. For example, a preferred boundary condition for the position of a key-light (or the sky of a light-map) is the frustum (or pyramid) defined by the ROI, especially plus a predefined space around the ROI (e.g., a bounding box), that is used as the apex of the pyramid, and the orientation or the direction towards the virtual camera (or a virtual observer). A spotlight and a fill-light can be placed anywhere, even within the volume.

Regarding a prioritization, there are many possibilities that depend on the medical scene shown in the image and the examination intended with the rendered image. The prioritization that can especially be adopted from photography. For example, the requirements, that a key-light should be illuminating the ROI from the upper right or that light in the direction of the camera view should be avoided to avoid flat images. Prioritizing a fill-light could be achieved by choosing the fill-light that is placed closest to the camera-to-subject axis (to avoid creating visible shadows). However, a prioritization could also be depending on the size or tinting of the shadows produced with this arrangement.

In praxis, prioritization may be performed by using frustums of the ROIs in the direction of the camera. Since the intersection of the frustums is usually not a single point, the vertex $v_i$ of the resulting intersection object may be picked in such a way that the light direction is not parallel to the view direction, to avoid flat images. For each vertex $v_i$ the average vector joining $v_i$ with each ROI may be computed, and the dot product of these vectors with the view direction may be computed as well. The smallest dot product may be chosen as highest priority. A directional light may be used for the key-light so the distance to the ROIs is not important.

The chosen arrangement can be outputted to a device rendering the 3D-image with shadows or used to render a 3D image directly, wherein it could also be regarded as an output when using the chosen arrangement by a rendering algorithm.

A system according to one embodiment for light arrangement for medical visualization, especially for controlling a medical imaging system to set the optimum light arrangement, includes the following components:

- a data interface designed to receive a medical 3D image, spatial information about a region of interest in this image and a virtual camera, and preferably information about a number of predefined artificial light sources,
- a determination unit (processor) designed for determining a plurality of possible arrangements for the light sources by using depth information based on the 3D image together with the spatial information about the region of interest in this image and the spatial information about the virtual camera, wherein valid arrangements are those where shadows on the region of interest are below a predefined threshold,
- a prioritization unit (processor) designed for prioritizing the determined arrangements,
- an output unit (user interface) designed for choosing the arrangement with the best prioritization and outputting the chosen arrangement.

The system may preferably additionally include a rendering unit (renderer) designed for rendering an image with shadows using the chosen arrangement of the light sources.

A control device (controller) according to one embodiment for controlling a medical imaging system includes a system described above. Alternatively, or additionally, the control device is designed to perform the method described above. The control device may include additional units or devices for controlling components of a medical imaging system.

A medical imaging system according to one embodiment, e.g., a magnetic resonance imaging system (MRI) or a computer tomography system (CT), includes a control device described above.

Summing up, the arrangement of the light sources controls the location of the shadows and highlights. However, shadows are also important, since shadows provide essential visual cues about the shapes, relative positions, and surface characteristics of objects. Shadows create a sense of depth, a key cue for capturing realistic looking images. But shadows can also hide important details of the data if the lights are not set properly. This is overcome by the selection of the best arrangement of light sources achieved by the embodiments.

Some units or modules of the system or the control device mentioned above can be completely or partially realized as software modules running on a processor of a system or a control device. A realization largely in the form of software modules can have the advantage that applications already installed on an existing system can be updated, with relatively little effort, to install and run these units of the present application. The object is also achieved by a computer program product with a computer program that is directly loadable into the memory of a device of a system or a control device of a medical imaging system, and which includes program units to perform the acts of the method when the program is executed by the control device or the system. In addition to the computer program, such a computer program product can also include further parts such as documentation and/or additional components, also hardware components such as a hardware key (dongle etc.) to facilitate access to the software.

A non-transitory computer readable medium such as a memory stick, a hard-disk, or other transportable or permanently-installed carrier can serve to transport and/or to store the executable parts of the computer program product so that these can be read from a processor unit (processor) of a control device or a system. A processor unit can include one or more microprocessors or their equivalents.

Particularly advantageous embodiments and features are given by the dependent claims, as revealed in the following description. Features of different claim categories may be combined as appropriate to give further embodiments not described herein.

Preferably, spatial information of the region of interest in the 3D-image is provided by automatic detection. Regarding an ROI, spatial information could especially be provided via a segmentation algorithm or using an eye tracking system which provides information about a focus of attention. Preferably, a ROI is identified based on user selection, automatic segmentation, data analysis, user gaze tracking, or 3D tracking of surgical instruments.

Preferably, after a first determination of a plurality of possible arrangements for the light sources, a number of further light sources are additionally provided and a second determination of a plurality of possible arrangements is performed for the additional light sources. This means preferably, that the arrangement of all light sources is determined (the light sources provided at the beginning and the newly added light sources, what is advantageous in the case when a good arrangement cannot be found). Preferably, a spotlight is added in the case that no position can be found for a certain ROI (e.g., if there is an ambient occlusion around an ROI). The spotlight should always be directed to the area with the most objectionable shadows.

A "good" arrangement is an arrangement in which all relevant ROIs (the ROI regarded by the method) are lighted while providing good overall lighting. A "good" light arrangement should, e.g., place the key light within the intersection of the frustums (each frustum defined by the ROI in the direction of the camera). If no such an arrangement exists, fill-lights are added for such ROIs that are not lighted well. The quality may be quantified by determining the intensity and/or area of shadows in an ROI and comparing that value with a predefined threshold value.

However, it could also be advantageous that the second determination is based on the number of arrangements determined by the first determination. This means, that the arrangements found for the light sources initially provided is not changed and only the newly added light sources are included as possible new arrangements in these initial arrangements. The total number of arrangements may be bigger than after the first determination, since for any "first arrangement" several arrangements of the newly added light sources could possibly be found.

Preferably, the act of prioritizing is performed based on guidelines from photography. It is preferred that a high priority is determined for a key-light or a sky of a light-map for positions (in the arrangements) above and towards the right side of the scene that illuminates most regions of interest. Alternatively, or additionally, a low priority is determined for key-light in the direction of the virtual camera (may, e.g., be valid for all light sources). This should be avoided to avoid flat images. Alternatively, or additionally, a high priority is given for a fill-light, when is placed closest to the camera-to subject axis, to avoid creating visible shadows. Alternatively, or additionally, a low priority is given for a light source from the front, unless it is the only way to light up all ROIs.

Preferably, at least one light source is a high-dynamic range (HDR) light probe. This is advantageous for enhancing realism by illuminating the scene and generating natural looking images. Alternatively, or additionally, at least one light source is an omnidirectional light source. This is advantageous for lighting shadows.

It is preferred to use an inverse illumination technique to automatically arrange a light source in the scene, especially to orient a light-map or place a key-light source. Regarding a region of interest, it is preferred to use the ROI centroid as the viewpoint with the frustum looking towards the camera position. Thus, for a region of interest, the centroid of the region of interest is calculated as a viewpoint, and a frustum is calculated looking towards a position of the virtual camera. The computed depth information is used to detect which light positions would generate shadows on the ROI.

For multiple ROIs, the process is repeated keeping track about which light positions illuminate most ROIs. For larger ROIs, a bounding box could be placed around the ROI and the method is repeated the process using the centroid or the visible corners of the bounding box. Thus, preferably, the method is performed for multiple regions of interest in the 3D image and/or for multiple disconnected objects forming one region of interest. Thus, light arrangement for a plurality of areas is determined. This is preferably performed by placing a bounding box around the regions of interest and/or the objects and repeating the determination act by using a centroid or visible corners of the bounding box.

Preferably, a light-map is used as light source. Such special embodiment of the light-map may be regarded as a non-changing setup of "internal" light sources or a fixed light distribution. The internal arrangement of lights or lighting of the light-map is preferably not changed by determining its arrangement, but different orientations of this light-map are determined in the search for valid (or "good") arrangements. Thus, in praxis, the light-map may be rotated so that the brighter part (usually the sky) points in the right direction. This may be done similar to the calculation of suitable key-light directions.

Preferably, a surgical instrument is a region of interest. This is especially advantageous when 3D tracking and positioning of this device is needed, especially for virtual reality, medical interventions and/or surgical planning simulations.

The method may also include elements of "cloud computing." In the technical field of "cloud computing," an IT infrastructure is provided over a data-network, e.g., a storage space or processing power and/or application software. The communication between the user and the "cloud" is achieved by data interfaces and/or data transmission protocols.

In the context of "cloud computing," in a preferred embodiment of the method, provision of data via a data channel (for example a data-network) to a "cloud" takes place. This "cloud" includes a (remote) computing system, e.g., a computer cluster that typically does not include the user's local machine. This cloud can be made available in particular by the medical facility, which also provides the medical imaging systems. In particular, the image acquisition data is sent to a (remote) computer system (the "cloud") via a RIS (Radiology Information System) or a PACS (Picture Archiving and Communication System).

Within the scope of a preferred embodiment of the system, the above-mentioned units are present on the "cloud" side. A preferred system further includes, a local computing unit (computer) connected to the system via a data channel (e.g., a data-network, particularly configured as RIS or PACS). The local computing unit includes at least one data receiving interface to receive data. Moreover, it is preferred if the local computer additionally has a transmission interface in order to send data to the system.

Overshadowing important areas is avoided. In medical visualization, many structures such as bones often cast shadows over other important structures. The proper setting of the light parameters is fundamental in generating images that provide a clear illustration of the complex anatomical structures.

Instead of generating balanced images with good contrast, the approach of the current embodiment is based on regions of interest within the volumetric data. One of the main objectives is to provide an optimal illumination to important anatomical structures in order to generate images useful for medical diagnosis or treatment.

BRIEF DESCRIPTION OF THE DRAWINGS

Other objects and features of the present invention will become apparent from the following detailed descriptions considered in conjunction with the accompanying drawings. It is to be understood, however, that the drawings are designed solely for the purposes of illustration and not as a definition of the limits of the invention.

In the diagrams, like numbers refer to like objects throughout. Objects in the diagrams are not necessarily drawn to scale.

DETAILED DESCRIPTION OF THE PREFERRED EMBODIMENTS

Figure 1:
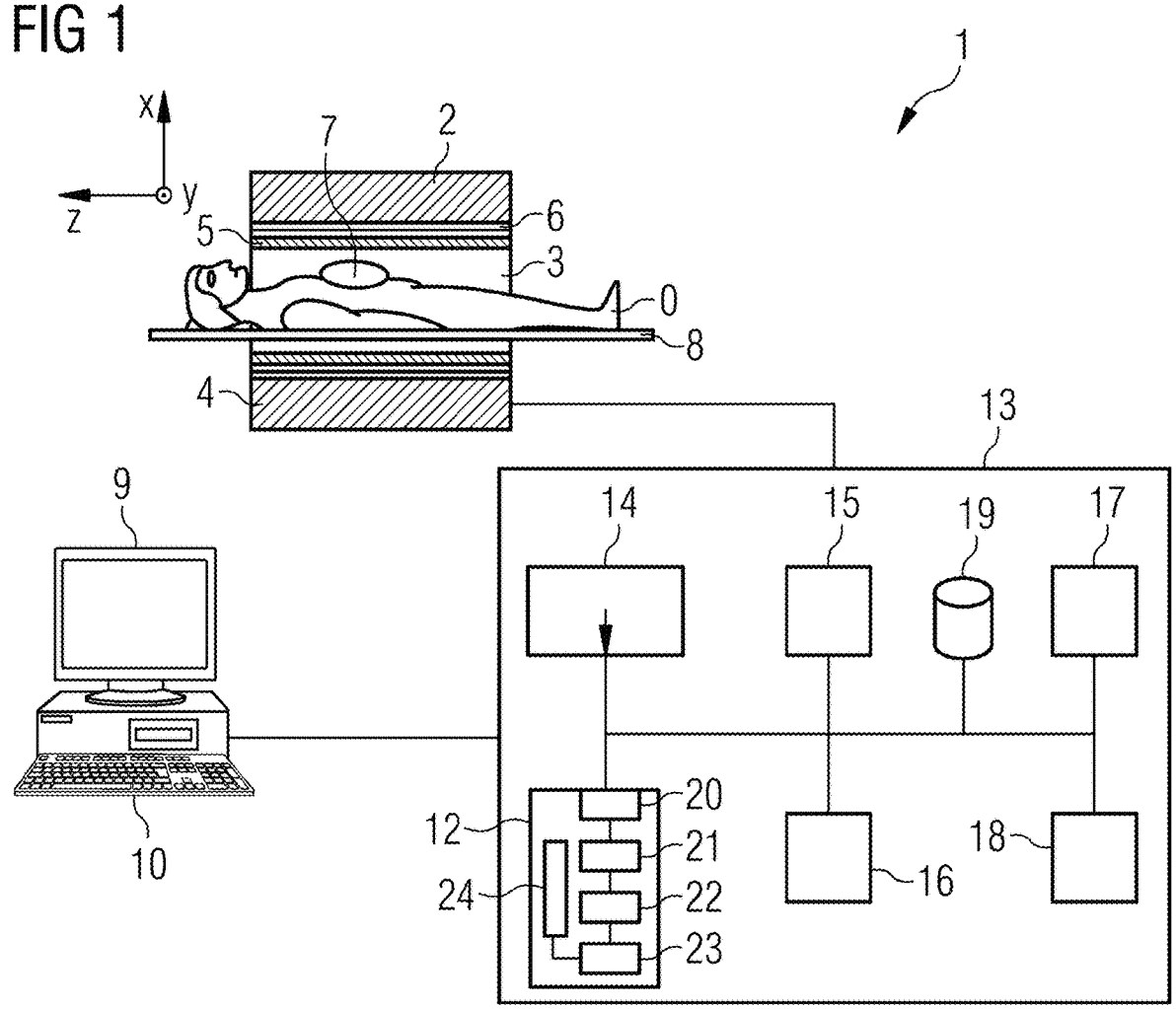
FIG. 1 shows a simplified MRI system with a system according to an embodiment.

FIG. 1 shows a schematic representation of a magnetic resonance imaging system 1 ("MRI-system"). The MRI system 1 includes the actual magnetic resonance scanner (data acquisition unit) 2 with an examination space 3 or patient tunnel in which a patient or test person is positioned on a driven bed 8, in whose body the actual examination object is located.

The magnetic resonance scanner 2 is typically equipped with a basic field magnet system 4, a gradient system 6 as well as an RF transmission antenna system 5 and an RF reception antenna system 7. In the shown exemplary embodiment, the RF transmission antenna system 5 is a whole-body coil permanently installed in the magnetic resonance scanner 2, in contrast to which the RF reception antenna system 7 is formed as multiple local coils for parallel imaging (symbolized here by only a single local coil) to be arranged on the patient or test subject.

The basic field magnet system 4 is designed in a typical manner so that it generates a basic magnetic field in the longitudinal direction of the patient, i.e., along the longitudinal axis of the magnetic resonance scanner 2 that proceeds in the z-direction. The gradient system 6 typically includes individually controllable gradient coils in order to be able to switch (activate) gradients in the x-direction, y-direction, or z-direction independently of one another.

The MRI system 1 shown here is a whole-body system with a patient tunnel into which a patient can be completely introduced. However, in principle other MRI systems, for example with a laterally open, C-shaped housing, as well as in smaller magnetic resonance scanners in which only one body part can be positioned, may be used.

In the following, we take an MRI system as an example for a medical imaging system. It is clear that besides MRI data, images from CT, ultrasound, or other medical imaging systems can be used.

Furthermore, the MRI system 1 has a central control device (controller) 13 that is used to control the MRI system 1. This central control device 13 includes a sequence control unit (sequencer) 14 for measurement sequence control. With this sequence control unit 14, the series of radio-frequency pulses (RF pulses) and gradient pulses can be controlled depending on a selected pulse sequence or, respectively, a series of multiple pulse sequence to acquire magnetic resonance images of the patient O within a measurement session. For example, such a series of pulse sequence can be predetermined within a measurement or control protocol. Different control protocols for different measurements or measurement sessions are typically stored in a memory 19 and can be selected by and operator (and possibly modified as necessary) and then be used to implement the measurement.

To output the individual RF pulses of a pulse sequence, the central control device 13 has a radio-frequency transmission device (transmitter) 15 that generates and amplifies the RF pulses and feeds them into the RF transmission antenna system 5 via a suitable interface (not shown in detail). To control the gradient coils of the gradient system 6, the control device 13 has a gradient system interface 16. The sequence control unit 14 communicates in a suitable manner with the radio-frequency transmission device 15 and the gradient system interface 16 to emit the pulse sequence.

Moreover, the control device 13 has a radio-frequency reception device (receiver) 17 (likewise communicating with the sequence control unit 14 in a suitable manner) in order to acquire magnetic resonance signals (i.e., raw data) for the individual measurements, which magnetic resonance signals are received in a coordinated manner from the RF reception antenna system 7 within the scope of the pulse sequence.

A reconstruction unit (computer) 18 receives the acquired raw data and reconstructs magnetic resonance image data therefrom for the measurements. This reconstruction is typically performed on the basis of parameters that may be specified in the respective measurement or control protocol. For example, the image data can then be stored in a memory 19.

Operation of the central control device 13 can take place via a terminal 10 with an input unit and a display unit 9, via which the entire MRI system 1 can thus also be operated by an operator. MR images can also be displayed at the display unit (display screen) 9, and measurements can be planned and started by the input unit (possibly in combination with the display unit 9), and in particular suitable control protocols can be selected (and possibly modified) with suitable series of pulse sequence as explained above.

The control device 13 includes a system 12 for automatic light arrangement for medical visualization designed to perform the method according to the invention. The system 12 includes the following components:

A data interface 20 designed to receive a medical 3D image D, here with depth information DI, spatial information about a region of interest R in this image and spatial information about a virtual camera C, and especially also information about a number of predefined artificial light sources L (e.g., from a memory or a user input; see the following figure explaining the method according to the invention). A number of lights can also be computed (in the course of the proceeding) based on the ROI and how well they are lit by an initial key-light. The data interface may also be used to send data outputted from the system 12. The data interface 20 may be designed to receive data from a user interface, a PACS or another data-line and may include different components designed to receive data via different data channels.

A determination unit 21 designed for determining a plurality of possible arrangements for the light sources L by using the depth information DI based on the 3D image D together with the spatial information about the region of interest R in this image and the spatial information about the virtual camera C, wherein valid arrangements are those where shadows S on the region of interest R are below a predefined threshold.

A prioritization unit 22 designed for prioritizing the determined arrangements.

An output unit 23 designed for choosing the arrangement with the best prioritization and outputting the chosen arrangement. The output unit may output the data via the data interface 20.

A rendering unit, designed to render an image lighted with the chosen arrangement of light sources and with shadows produced by the lighting, e.g., with well-known rendering procedures.

The components of the system preferably appear to be software modules.

The MRI system 1 according to one embodiment, and in particular the control device 13, can have a number of additional components that are not shown in detail but are typically present at such systems, for example a network interface in order to connect the entire system with a network and be able to exchange raw data and/or image data or, respectively, parameter maps, but also additional data (for example patient-relevant data or control protocols).

The manner by which suitable raw data are acquired by radiation of RF pulses and the generation of gradient fields, and MR images are reconstructed from the raw data, is known to those skilled in the art and thus need not be explained in detail herein.

Figure 2:
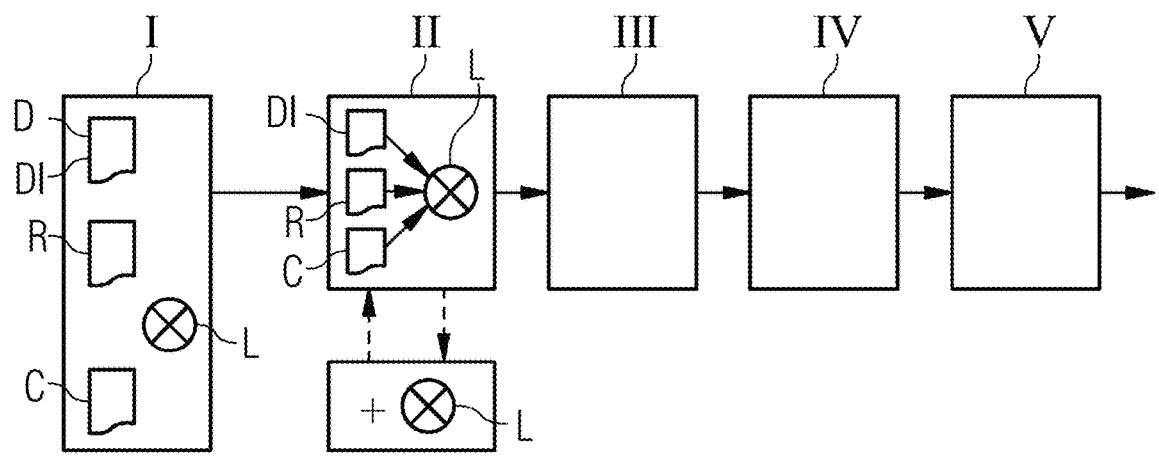
FIG. 2 shows a block diagram of the process flow of a preferred method.

FIG. 2 shows a block diagram of the process flow of a preferred method for automatic light arrangement for medical visualization according to the invention.

In act I, a medical 3D image D, here with depth information DI, spatial information about a region of interest R in this 3D-image D and spatial information about a virtual camera C is provided. This can be done by a user input, access to image data via PACS or measurements in the 3D image. More than one region if interest can be chosen, e.g., an organ and a surgical instrument.

It should be noted that since a rendering of a (digital) image is the aim, the region of interest R as well as the virtual camera C are only datasets relative to this 3D image D.

Spatial information of the region of interest R in the 3D-image D could especially be provided by automatic detection, preferably by detecting an area based on automatic segmentation, data analysis, user gaze tracking, or 3D tracking of surgical instruments, especially wherein an area of high curvature is detected and defined as region of interest, preferably via a segmentation algorithm, or using an eye tracking system.

In addition, information about a number of predefined artificial light sources L is provided, i.e., information what type of light sources and how many light sources of a type should be used. This provision may be realized by reading data from a memory (e.g., RAM, EEPROM, hard disk, MMC), especially by preferences, calculating data or by user input. For example, at least one light source L is a high-dynamic range light probe and/or an omnidirectional light source. Also, a light-map can be used as light source L. A three-point lighting is preferred.

In act II, a plurality of possible arrangements of the light sources L is determined by using the depth information based on the 3D image DI together with the spatial information about the region of interest R in this image and the spatial information about the virtual camera C. Valid arrangements are those where shadows S on the region of interest R are below a predefined threshold.

In this example, there is the possibility (see box below act II with the two dashed arrows) that after a first determination of a plurality of possible arrangements for the light sources L, a number of further light sources L, especially a spotlight, can additionally be provided and a second determination of a plurality of possible arrangements is performed for the additionally provided number of light sources L. The second determination may be based on the number of arrangements determined by the first determination.

Preferably, an inverse illumination technique can be applied to automatically arrange a light source L, preferably to orient a light-map or to place a key-light source. Such inverse illumination technique is well known in the art usually used to infer information from images. For a region of interest R, the centroid of the region of interest can be calculated as a viewpoint and a frustum can be calculated looking towards a position of the virtual camera C.

In act III, the determined arrangements are prioritized. The act of prioritizing is performed based on guidelines from photography.

Possible guidelines for a high priority are
a) (for a key-light or a sky of a light-map) to have a position above and towards the right side of the scene that illuminates most of the region of interest, or
b) (for a fill-light) being placed closest to a camera-to-subject axis.

Possible guidelines for a low priority are
a) a light shining in the direction of the virtual camera, or
b) a light source shines from the front on the ROI, unless it is the only way to light up all regions of interest.

In act IV, the arrangement with the best prioritization is chosen from the determined arrangements.

In act V, an image is rendered with shadows based on the chosen arrangement of light sources.

The method may be performed for multiple regions of interest R, R1 (see e.g., FIG. 5) in the 3D image D, preferably by placing a bounding box B around the regions of interest R, R1 and repeating the determination act by using a centroid or visible corners of the bounding box B.

Figure 3:
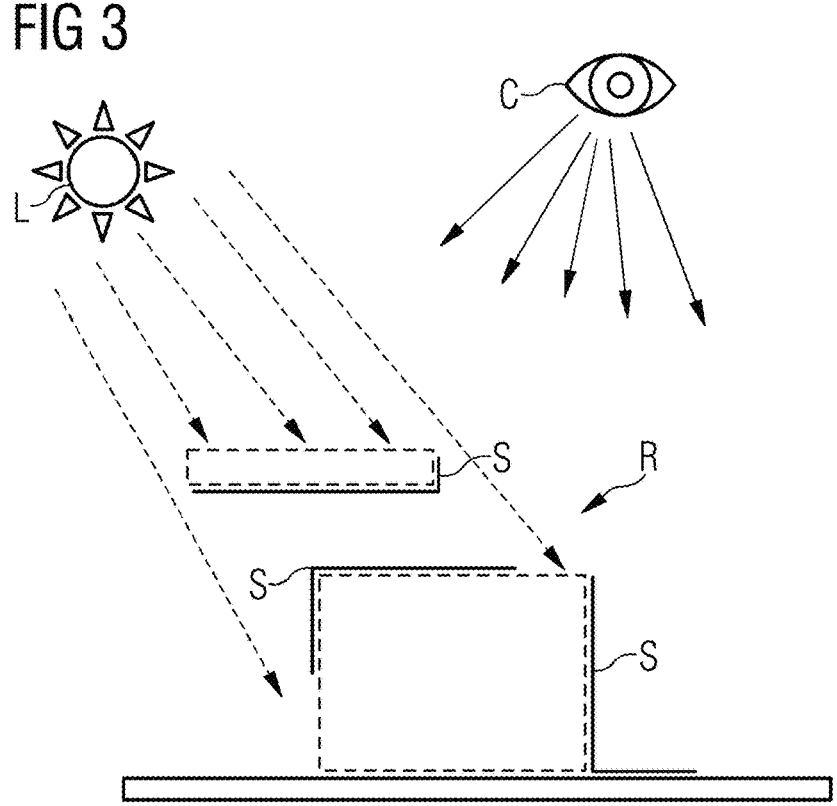
FIG. 3 shows an illumination example.

FIG. 3 shows an illumination example. A region of interest including two different objects (dashed boxes) is illuminated by a light source L and watched by a virtual camera C. As can be seen by the thick black lines, shadows S are generated when objects are completely or partially occluded from a light source L.

Figure 4:
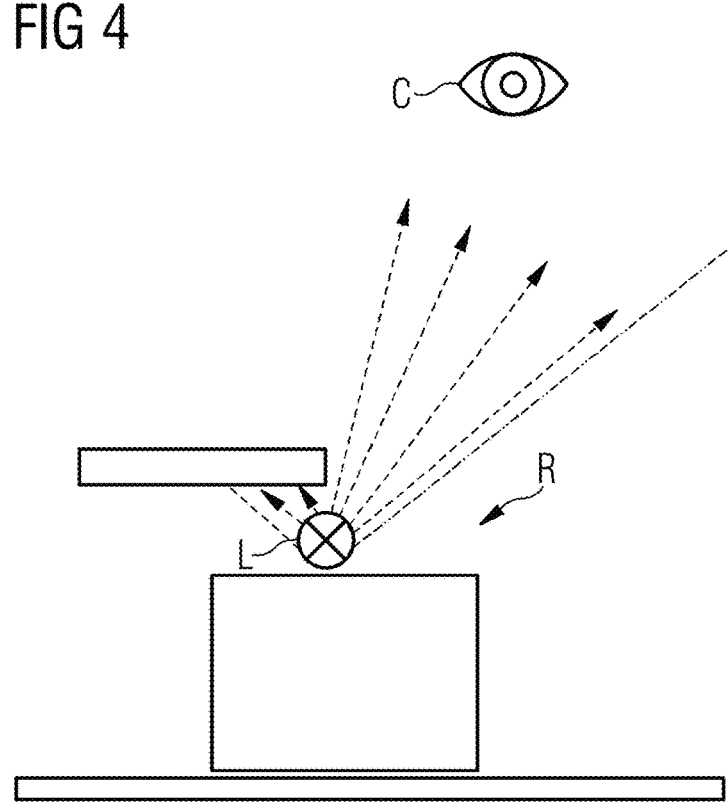
FIG. 4 shows an example inverse illumination based on a ROI position.

FIG. 4 shows an Inverse illumination based on a ROI position. This inverse illumination technique is used to automatically orient a light-map or place a key-light source in the scene (i.e., arranging a light source).

Figure 5:
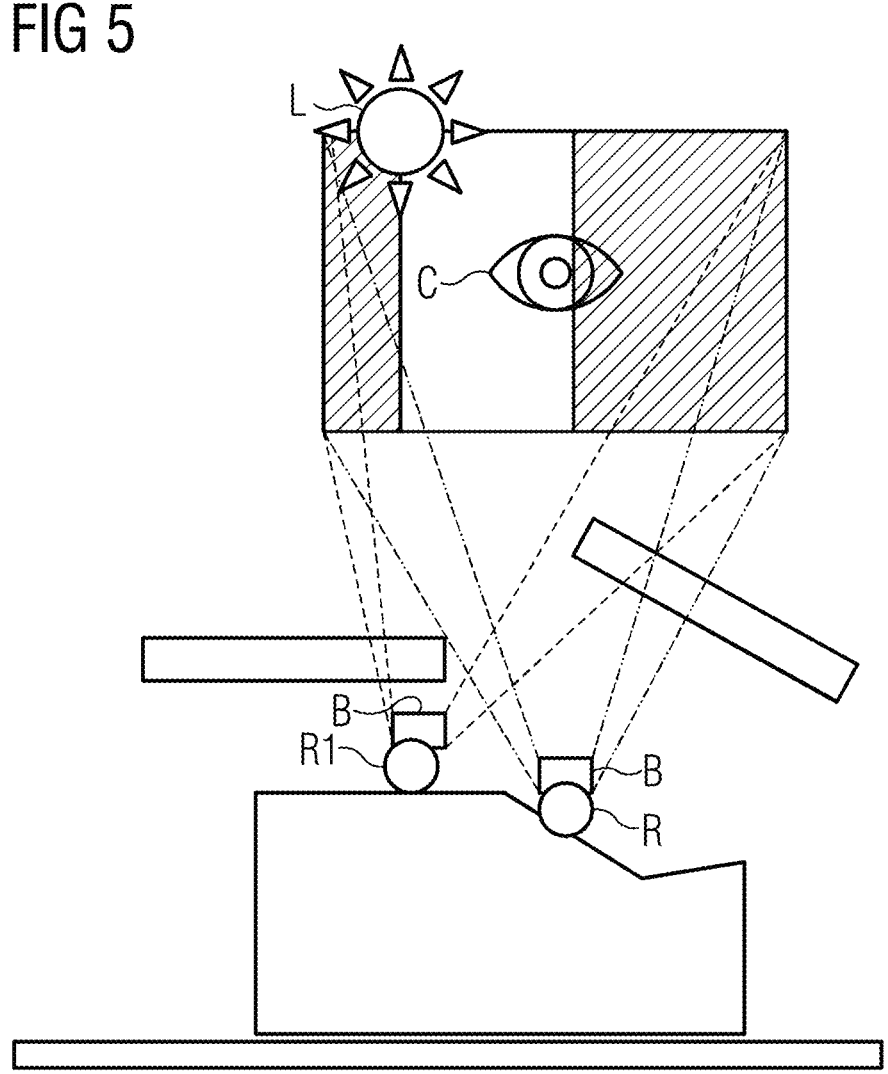
FIG. 5 shows example frustums used for light design of two given ROI.

FIG. 5 shows two regions of interest R (circles). During an initial act, the ROI centroid are used as the viewpoint, with the frustum looking towards the virtual camera C. The computed depth information is used to detect which light positions would generate shadows on a ROI. For the second ROI, the process is repeated keeping track which light positions illuminate most of the two ROIs. For larger ROIs, a bounding box B (as shown here) could be placed around the ROIs and the method can be performed using the centroid or the visible corners of the bounding box.

Once the potential arrangements of the light sources are determined, they can be prioritized following the guidelines form photography. For instance, a front-light should be avoided unless it is the only way to light up all ROIs. Using these guidelines, highest priority is given to positions above and towards the right side of the scene that illuminates most of the given ROIs.

FIGS. 6 to 11 illustrate results of different arrangements of light sources L. In all these figures, the same image, showing the vessels around the neck as the ROI, is rendered with differently arranged lights.

Figure 6:
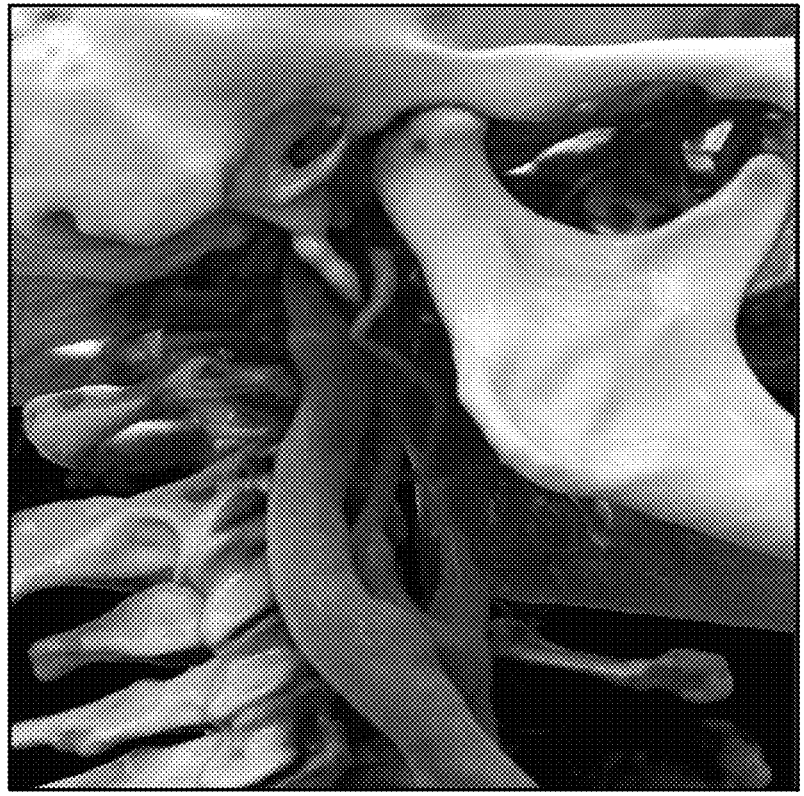
FIG. 6 shows an example rendered image lighted by a light map.

FIG. 6 shows an image that is rendered by using a default light-map to illuminate the scene with the sky on top. Although light maps illuminate the scene in almost all directions, the vasculature around the neck still looks quite dark for diagnostic purposes.

Thus, it can be seen that even with these omnidirectional lights, some areas of the volume could remain hidden by shadows. For instance, the vasculature around the neck is indistinguishable because of shadows cast by the jawbone. Although this image has good balance of highlights, midtones, and shadow areas, it is ineffective for an accurate diagnosis of the patients with a vascular condition.

Figure 7:
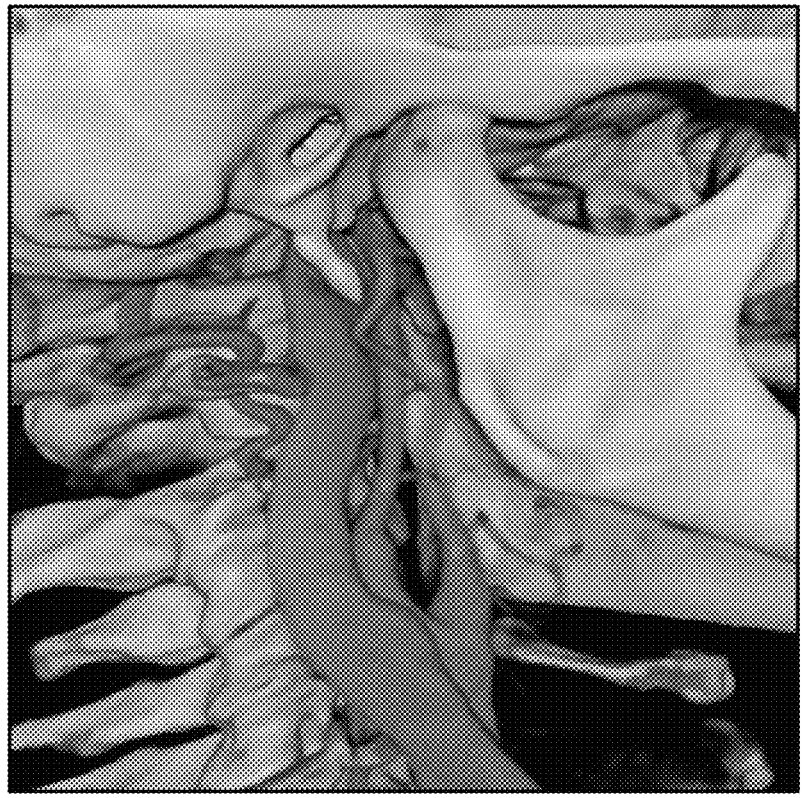
FIG. 7 shows an example rendered image lighted by front lighting.

FIG. 7 shows a rendered image using front lighting. This configuration generates no occluding shadows, but the resulting image is quite flat.

Figure 8:
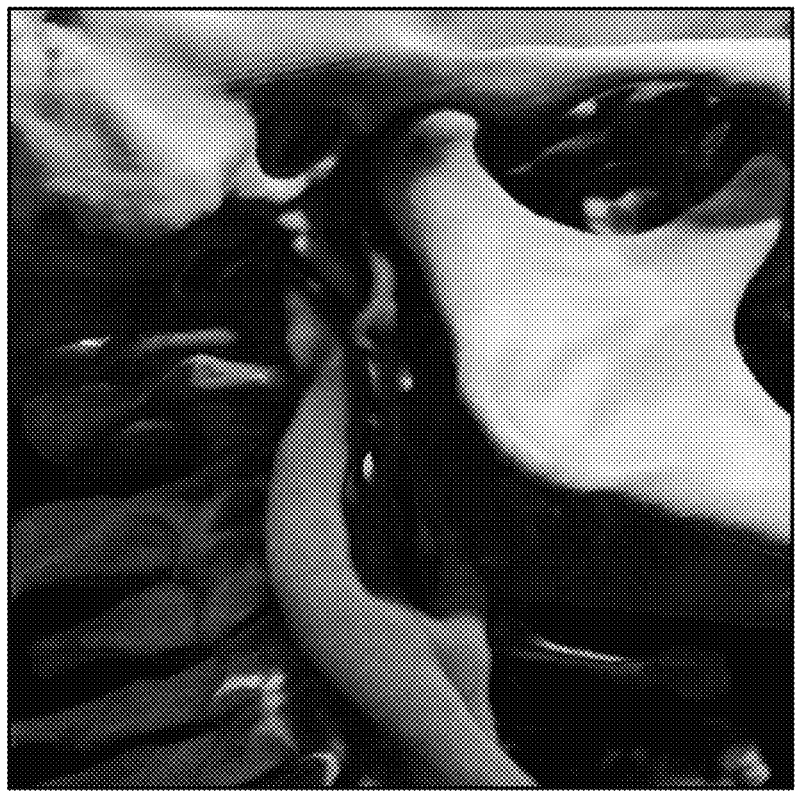
FIG. 8 shows an example rendered image lighted by upper right lighting.

FIG. 8 shows a rendered image lighted by upper right lighting, producing a quite good 3d-look, but severe shadows.

Figure 9:
FIG. 9 shows an example rendered image lighted by a light map and a key-light.

FIG. 9 shows a rendered image is generated by placing a light map with sky on top and a key-light to illuminate the vasculature, avoiding hard shadows on the ROI.

Figure 10:
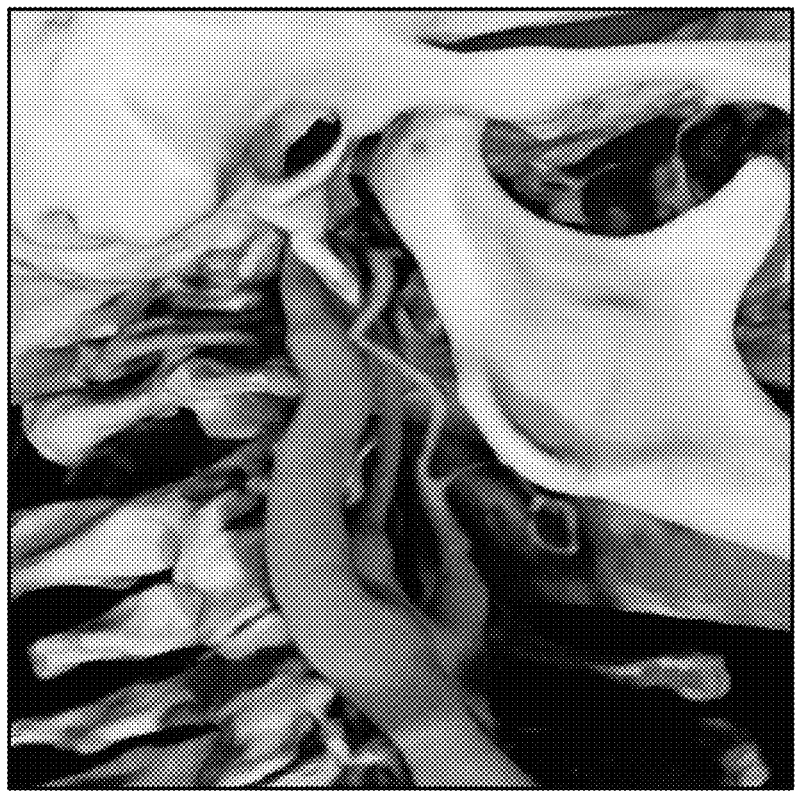
FIG. 10 shows an example rendered image lighted by a light map, a key-light and a fill-light.

FIG. 10 shows a rendered image lighted by a light map, a key-light, and a fill-light. The image uses the same configuration as FIG. 9, plus a fill-light to make the shadows appear softer.

Figure 11:
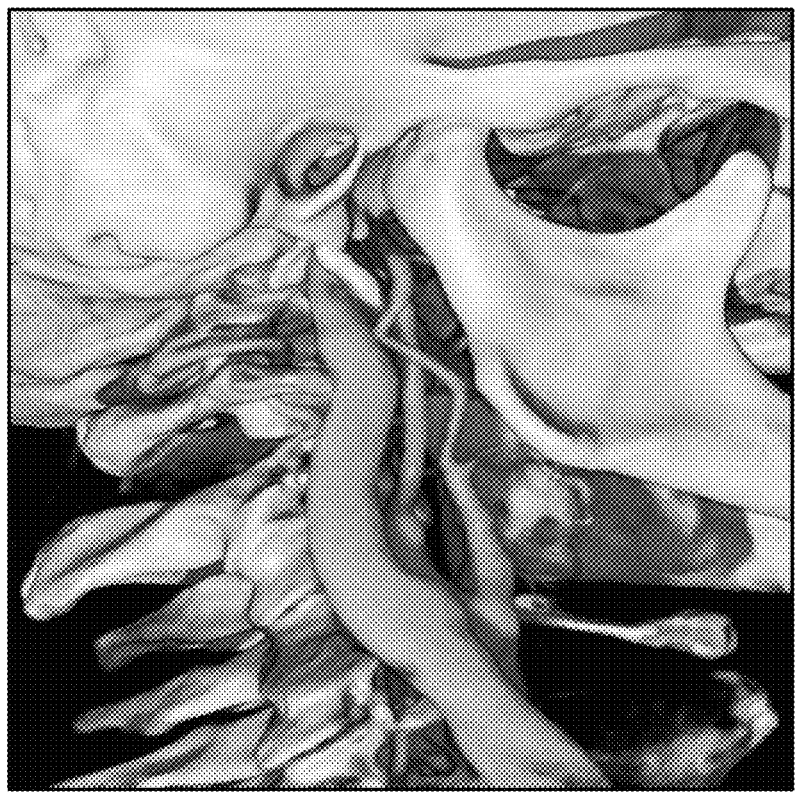
FIG. 11 shows an example rendered image lighted by a light map, a key-light and a spotlight, FIG. 12, two ROIs with frustums used during inverse illumination in one embodiment.

FIG. 11 shows a rendered image lighted by a light map, a key-light, and a spotlight. The image uses the same configuration as FIG. 9, plus a spotlight placed within the skull to illuminate the back of the given ROI, creating a glowing effect.

Occasionally, ambient occlusions can be found around an ROI since there is no guarantee that a configuration exists in which all (the entire) ROIs can be illuminated by the key-light. The configuration of FIG. 7, in which the key-light lies behind the camera, provides less shadows, but this configuration should be avoided, since it generates flat images. A key-light from the upper right (FIG. 8) or a lighting as in FIG. 6 provides a good 3D impression, but severe shadows occluding important areas. In order to brighten these occluded areas, a spotlight or a fill-light can be used.

Ambient occlusion for the ROIs can be approximated based on the depth map from the camera view. When the ambient occlusion is found to be significant, a spotlight can be placed behind the ROI (see FIG. 11).

Figure 12:
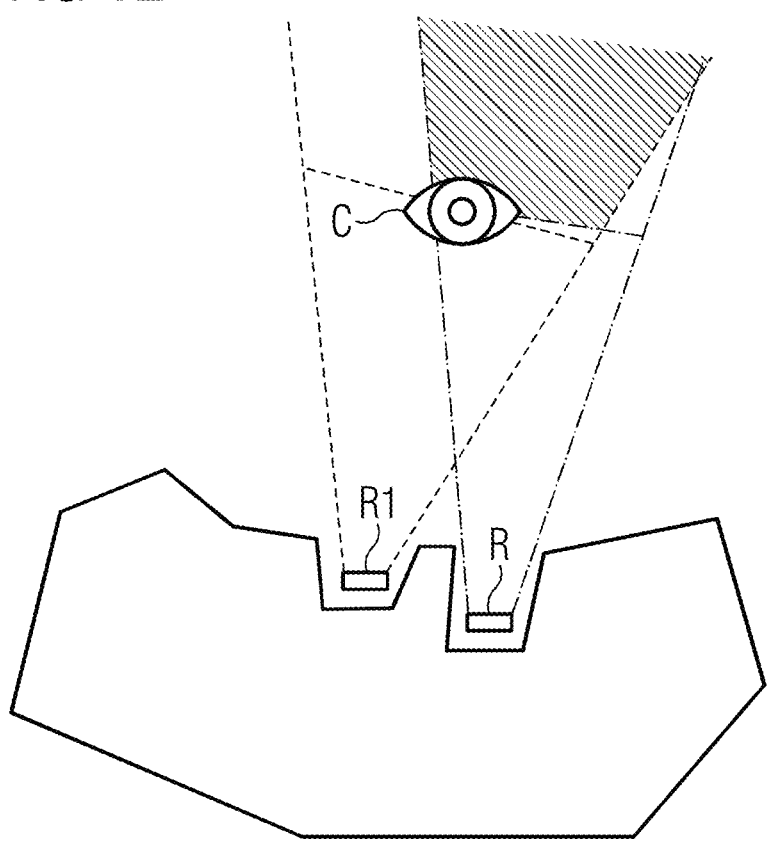

In FIG. 12, two ROIs are shown together with their frustums. For a better overview, the scene is shown from above. Prioritization may be performed by using frustums of the ROIs in the direction of the camera. Since the intersection of the frustums is usually not a single point, the vertex $v_i$ of the resulting intersection object may be picked in such a way that the light direction is not parallel to the view direction, to avoid flat images. For each vertex $v_i$, the average vector joining $v_i$ with each ROI may be computed, and the dot product of these vectors with the view direction may be computed as well. The dot product in the vicinity of 0.707 may be chosen as highest priority. This corresponds to angles degrees between the light and the camera closer to 45. A directional light may be used for the key-light so the distance to the ROIs is not important.

Although the present invention has been disclosed in the form of preferred embodiments and variations thereon, it will be understood that numerous additional modifications and variations could be made thereto without departing from the scope of the invention. For the sake of clarity, it is to be understood that the use of "a" or "an" throughout this application does not exclude a plurality, and "comprising" does not exclude other acts or elements. The mention of a "unit" or a "device" does not preclude the use of more than one unit or device.

The invention claimed is:

1. A method for automatic light arrangement for medical visualization, the method comprising:
providing a medical 3D image,
providing spatial information about a region of interest in the medical 3D image and spatial information about a virtual camera,
determining a plurality of arrangements for light sources using depth information based on the medical 3D image together with the spatial information about the region of interest in the medical 3D image and the spatial information about the virtual camera, wherein valid arrangements of the plurality of arrangements are arrangements where shadows on the region of interest are below a predefined threshold,
prioritizing the determined arrangements, and
choosing the arrangement with a greatest prioritization.

2. The method according to claim 1, wherein the spatial information of the region of interest in the medical 3D image is provided by automatic detection.

3. The method according to claim 2 wherein the automatic detection comprises detecting an area based on automatic segmentation, data analysis, user gaze tracking, or 3D tracking of surgical instruments, wherein an area of high curvature is detected and defined as region of interest via data analysis.

4. The method according to claim 1, wherein after a first determination of a plurality of arrangements for the light sources, a number of further light sources is provided in addition to the determined arrangements of the light sources and a second determination of a plurality of arrangements is performed for the additionally provided number of light sources.

5. The method according to claim 4 wherein one of the further light sources comprises a spotlight, wherein the second determination is based on a number of arrangements determined by the first determination.

6. The method according to claim 1, wherein prioritizing is performed based on guidelines from photography.

7. The method according to claim 6, wherein the guidelines from photography include where:
a key-light or a sky of a light-map for positions above and towards a right side of a scene that illuminates the region of interest or a fill-light that is placed closest to a camera-to-subject axis are assigned a higher priority than either or
a light source from a front, unless the light source being from the front is an only way to light up all regions of interest.

8. The method according to claim 1, wherein at least one light source is a high-dynamic range light probe and/or an omnidirectional light source.

9. The method according to claim 1, wherein the method is performed for multiple regions of interest in the medical 3D image and/or for multiple disconnected objects forming one region of interest, by placing a bounding box around the regions of interest and/or the multiple disconnected objects and repeating the determination act by using a centroid or visible corners of the bounding box.

10. The method according to claim 1, wherein a light-map is used as one of the light sources, the light-map having a fixed light distribution, and wherein an internal arrangement of lights or lighting of the light-map is not changed by determining its arrangement, but different orientations of this light-map are determined in a search for arrangements.

11. The method according to claim 1, wherein an inverse illumination technique is applied to automatically orient a light-map or to place a key-light source.

12. The method according to claim 1, wherein for the region of interest, a centroid of the region of interest is calculated as a viewpoint and a frustum is calculated looking towards a position of the virtual camera.

13. The method according to claim 1, wherein a surgical instrument is the region of interest.

14. The method according to claim 1, further comprising providing information about a number of predefined artificial light sources.

15. A system for automatic light arrangement for medical visualization, the system comprising:
a data interface configured to receive a medical three-dimensional (3D) image, spatial information about a region of interest in the medical 3D image, spatial information about a virtual camera, and information about a number of predefined artificial light sources, and
a processor configured to: determine a plurality of possible arrangements for the light sources using depth information based on the medical 3D image together with the spatial information about the region of interest and the spatial information about the virtual camera, wherein valid arrangements of the possible arrangements are those where shadows on the region of interest are below a predefined threshold, the processor configured to prioritize the possible arrangements, and the processor configured to choose the arrangement from the valid arrangements with the best prioritization and output the chosen arrangement.

16. The system of claim 15 wherein the processor is a controller of a medical imaging system.

17. A non-transitory computer-readable medium on which is stored instructions that can be read and executed by a processor, the instructions comprising:
determining a plurality of arrangements for light sources using depth information based on a medical three-dimensional (3D) image together with spatial information about a region of interest in the medical 3D image and spatial information about a virtual camera, wherein: valid ones of the arrangements are those where shadows on the region of interest are below a predefined threshold and the determination of the arrangements is based on a number of predefined perceptual metrics applied specifically to the regions of interest,
prioritizing the determined arrangements, and
choosing the arrangement with a greatest prioritization.

18. The method of claim 1, wherein the determination of the arrangements is further based on a number of predefined perceptual metrics applied specifically to the regions of interest.

* * * * *